United States Patent
Sato (10) Patent No.: US 11,471,119 B2
(45) Date of Patent: Oct. 18, 2022

(54) ANALYSIS DEVICE AND ANALYSIS METHOD

(71) Applicant: Shimadzu Corporation, Kyoto (JP)

(72) Inventor: Kenji Sato, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 76 days.

(21) Appl. No.: 17/175,936

(22) Filed: Feb. 15, 2021

(65) Prior Publication Data

US 2021/0369220 A1 Dec. 2, 2021

(30) Foreign Application Priority Data

Jun. 2, 2020 (JP) .............................. JP2020-096247

(51) Int. Cl.
*G01N 23/207* (2018.01)
*A61B 6/00* (2006.01)

(52) U.S. Cl.
CPC .......... *A61B 6/4441* (2013.01); *A61B 6/4233* (2013.01); *A61B 6/4291* (2013.01); *A61B 6/584* (2013.01); *A61B 6/588* (2013.01)

(58) Field of Classification Search
CPC .......... G01N 23/207; G01N 2223/076; G01N 23/2209; G01N 6/4441; G01N 2223/1016; G01N 2223/501; G02N 2223/303; A61B 6/4291; A61B 6/584; A61B 6/4233
See application file for complete search history.

(56) References Cited

U.S. PATENT DOCUMENTS

2017/0160213 A1   6/2017  Sato et al.
2020/0225173 A1*  7/2020  Sato .................. G01N 23/2209

FOREIGN PATENT DOCUMENTS

JP   2002-214165 A    7/2002
JP   2017-223638 A   12/2017

OTHER PUBLICATIONS

The website https://www.an.shimadzu.co.jp/surface/xd/onesight.htm downloaded Nov. 5, 2020 (searched on Dec. 3, 2019).
Sato et al., "Evaluation of Analytical Precision of Polychromatic Simultaneous WDXRF Spectrometer and Application to Valence Analysis of Cathode Materials of Lithium-Ion Batteries," ACS Analytical Chemistry, 2020, 92, pp. 758-765, Dec. 10, 2019.

(Continued)

*Primary Examiner* — Don K Wong
(74) *Attorney, Agent, or Firm* — Muir Patent Law, PLLC (57) ABSTRACT

A valence of a target element of a sample and crystallinity of a sample can be detected with a small device. The analysis device 100 includes: a placement holder 110 for placing a sample S; an X-ray source 11 for irradiating the sample S with X-rays; a first detector 141 for detecting characteristic X-rays generated from the sample S by the irradiation of the X-rays; a second detector 142 for detecting X-rays diffracted by the sample; and a signal processing device 20. The signal processing device 20 detects the valence of the target element of the sample based on the characteristic X-rays detected by the first detector 141, and detects the crystallographic data of the sample based on the X-rays detected by the second detector 142.

15 Claims, 7 Drawing Sheets

(56) References Cited

OTHER PUBLICATIONS

Adachi et al., "Development of Polychromatic Simultaneous Wavelength Dispersive X-Ray Fluorescence Spectrometer (PS-WDXRF)", Reprinted from Shimadzu Review, vol. 75, No. 3,4 (2018) pp. 85-93, submitted with a machine tanslation.

Ito et al., "In situ X-ray absorption spectroscopic study of Li-rich layered cathode material Li[Ni0.17Li0.2Co0.07Mn0.56] O2", Journal of Power Sources, 196 (2011) pp. 6828-6834.

* cited by examiner

ANALYSIS DEVICE AND ANALYSIS METHOD

CROSS-REFERENCE TO RELATED APPLICATIONS

This application claims priority under 35 U.S.C. § 119 to Japanese Patent Application No. 2020-096247 filed on Jun. 2, 2020, the entire disclosure of which is incorporated herein by reference in its entirety.

BACKGROUND OF THE INVENTION

Field of the Invention

The present disclosure relates to an analysis device and an analysis method.

Description of Related Art

For example, Patent Document 1 discloses a device in which element-specific characteristic X-rays generated from a sample are detected by using a radiation X-ray light source provided in a large radiation facility SPring-8 (Super Photon ring-8 GeV) to detect an electronic structure or the like of a compound formed by elements contained in a sample.

PRIOR ART DOCUMENT

Patent Document

Patent Document 1: Japanese Unexamined Patent Application Publication No. 2002-214165

SUMMARY OF THE INVENTION

Problems to be Solved by the Invention

A radiant X-ray source installed in a large radiant facility may be used to detect a valence of an element contained in a sample and crystallinity of a sample together. There is also a need for detecting a valence of a sample and crystallinity of a sample with a small device.

The present invention has been made to solve such problems, and an object of the present invention is to provide a technique for detecting a valence of a target element of a sample and crystallinity of a sample with a small device.

Means for Solving the Problem

An analysis device of the present disclosure includes: a placement stand configured to place a sample thereon; an X-ray source configured to emit X-rays to a sample; a first detector configured to detect characteristic X-rays generated from the sample by X-ray irradiation; a second detector configured to detect X-rays diffracted by the sample; and a signal processing device. The signal processing device is configured to detect a valence of a target element of the sample based on the characteristic X-ray detected by the first detector and detect crystallographic data of the sample based on the X-rays detected by the second detector.

Effects of the Invention

According to the present disclosure, it is possible to detect a valence of a target element of a sample and crystallinity of a sample with a small device.

BRIEF DESCRIPTION OF THE DRAWINGS

The preferred embodiments of the present invention are shown by way of example, and not limitation, in the accompanying figures.

EMBODIMENTS FOR CARRYING OUT THE INVENTION

Hereinafter, some embodiments of the present invention will be described in detail by referring to the attached drawings. The same or corresponding portion in the drawing is denoted by the same reference numeral, and the description thereof will not be repeated.

<Configuration of Analysis Device>

Figure 1:
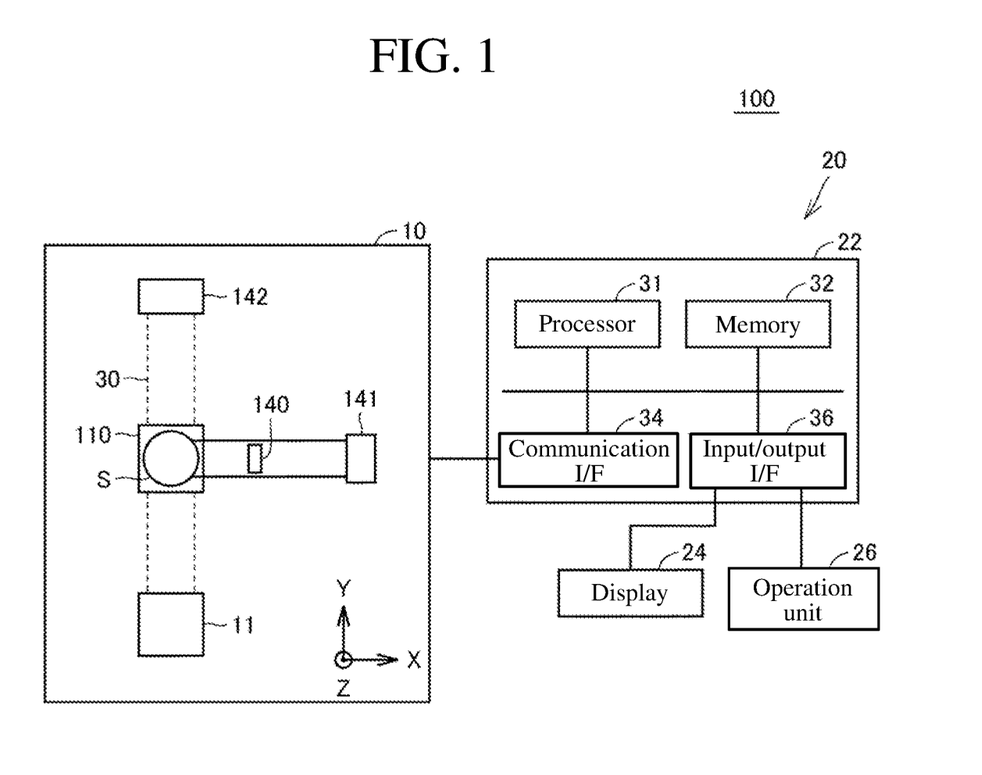
FIG. 1 is a diagram showing a configuration example of an analysis device 100 according to this embodiment.

FIG. 1 is a diagram showing a configuration example of an analysis device 100 according to this embodiment. The analysis device 100 has a device body 10 and a signal processing device 20. The analysis device 100 is generally a device in which an X-ray diffractometer (XRD: X-Ray Diffraction) for analyzing the crystalline state of a sample as an analysis target, and a wavelength-dispersive X-ray fluorescence analysis device for analyzing elements contained in a sample by observing the characteristic X-rays generated from a sample as an analysis target are integrated.

First, the device body 10 will be described. The device body 10 is provided with an X-ray source 11, a sample holder 110, a goniometer 30, a dispersive crystal 140, a first detector 141, and a second detector 142. The goniometer 30 corresponds to the "driving unit" of this embodiment. The goniometer 30 drives the X-ray source 11 and the second detector 142 to satisfy the predetermined positional relation to be described later. A sample S is placed on the sample holder 110. In the analysis device 100, the sample S as the analysis target is basically a solid-state sample to perform both the X-ray diffraction and the wavelength-dispersive X-ray fluorescence analysis.

In this specification, the plane on which the sample S is arranged is defined as an X-Y plane, and the direction perpendicular to the X-Y plane is defined as a Z-axis direction. Further, the X-ray source 11 and the sample holder 110 are configured to be common in the X-ray diffractometer and the wavelength-dispersive X-ray fluorescence analysis device.

The X-ray source 11 irradiates the sample S with X-rays. When the sample S is irradiated with X-rays, characteristic X-rays are generated from the sample S. The characteristic X-rays and fluorescent X-rays are synonymous. The characteristic X-rays generated from the sample S are dispersed by a dispersive crystal 140 and then detected by the first detector 141. The first detector 141 has a plurality of detection elements 151. By analyzing at which detection element of the first detector 141 the characteristic X-rays were detected, the element contained in the sample S is identified. That is, a wavelength-dispersive fluorescent X-ray analysis device is composed of the dispersive crystal 140 and the first detector 141.

When the sample S is irradiated with X-rays, the X-rays are diffracted by the sample S. The diffracted X-rays are referred to as "diffracted X-rays". The diffracted X-rays generated by the sample S are detected by the second detector 142. The crystalline state of the sample S can be detected by analyzing the diffracted X-rays detected by the second detector 142 while changing the irradiation angle of the X-rays emitted from X-ray source 11 to the sample S using the goniometer 30. That is, the X-ray diffractometer is configured by the goniometer 30 and the second detector.

Further, in the example of FIG. 1, when the analysis device 100 is viewed in a plane view in the X-Y plane, the line connecting the center of the sample holder 110 and the center of the first detector 141 and the line connecting the center of the sample holder 110 and the center of the second detector 142 meet at a right angle. Thus, the effect due to the incident of the diffracted X-ray on the first detector 141 and the effect due to the incident of the characteristic X-rays dispersed by the dispersive crystal 140 on the second detector 142 can be reduced.

Next, the signal processing device 20 will be described. The detection signal corresponding to the characteristic X-rays detected by the device body 10 and the detection signal corresponding to the diffracted X-rays are transmitted to the signal processing device 20. The signal processing device 20 has a controller 22, a display 24, and an operation unit 26. The signal processing device 20 controls the operation of the device body 10. The signal processing device 20 is also configured to analyze the detection signal transmitted from the device body 10 and display the result based on the analysis on the display 24.

The controller 22 has, as its main components, a processor 31, a memory 32, a communication interface (I/F) 34, and an input/output I/F 36. These units are connected to each other via a bus to be able to communicate with each other.

The processor 31 is typically an arithmetic processing unit, such as, e.g., a CPU (Central Processing Unit) and an MPU (Micro Processing Unit). The processor 31 controls the operation of each unit of the analysis device 100 by reading and performing the programs stored in the memory 32. Specifically, by performing the programs, the processor 31 realizes processing, such as, analyzing the characteristic X-ray data, based on the characteristic X-rays detected by the first detector 141 and the diffracted X-ray data based on the diffracted X-rays detected by the second detector 142. In the example of FIG. 1, a configuration in which the processor is configured by a single processor is illustrated, but the controller 22 may be configured to include a plurality of processors.

The memory 32 is realized by a non-volatile memory, such as, e.g., a RAM (Random Access Memory), a ROM (Read Only Memory), and a flash memory. The memory 32 stores programs to be performed by the processor 31 or data to be used by the processor 31.

The input/output I/F 36 is an interface for exchanging various types of data between the processor 31 and the display 24 and the operation unit 26.

The communication I/F 34 is a communication interface for exchanging various types of data with the device body 10, and is implemented by adapters, connectors, and the like. The communication method may be a wireless communication method, such as, e.g, a wireless LAN (Local Area Network), and a wired communication method using a USB (Universal Serial Bus).

To the controller 22, the display 24 and the operation unit 26 are connected. The display 24 is composed of a liquid crystal panel capable of displaying images. The operation unit 26 accepts an operation input by a user to the analysis device 100. The operation unit 26 is typically composed of a touch panel, a keyboard, a mouse, and the like.

Figure 2:
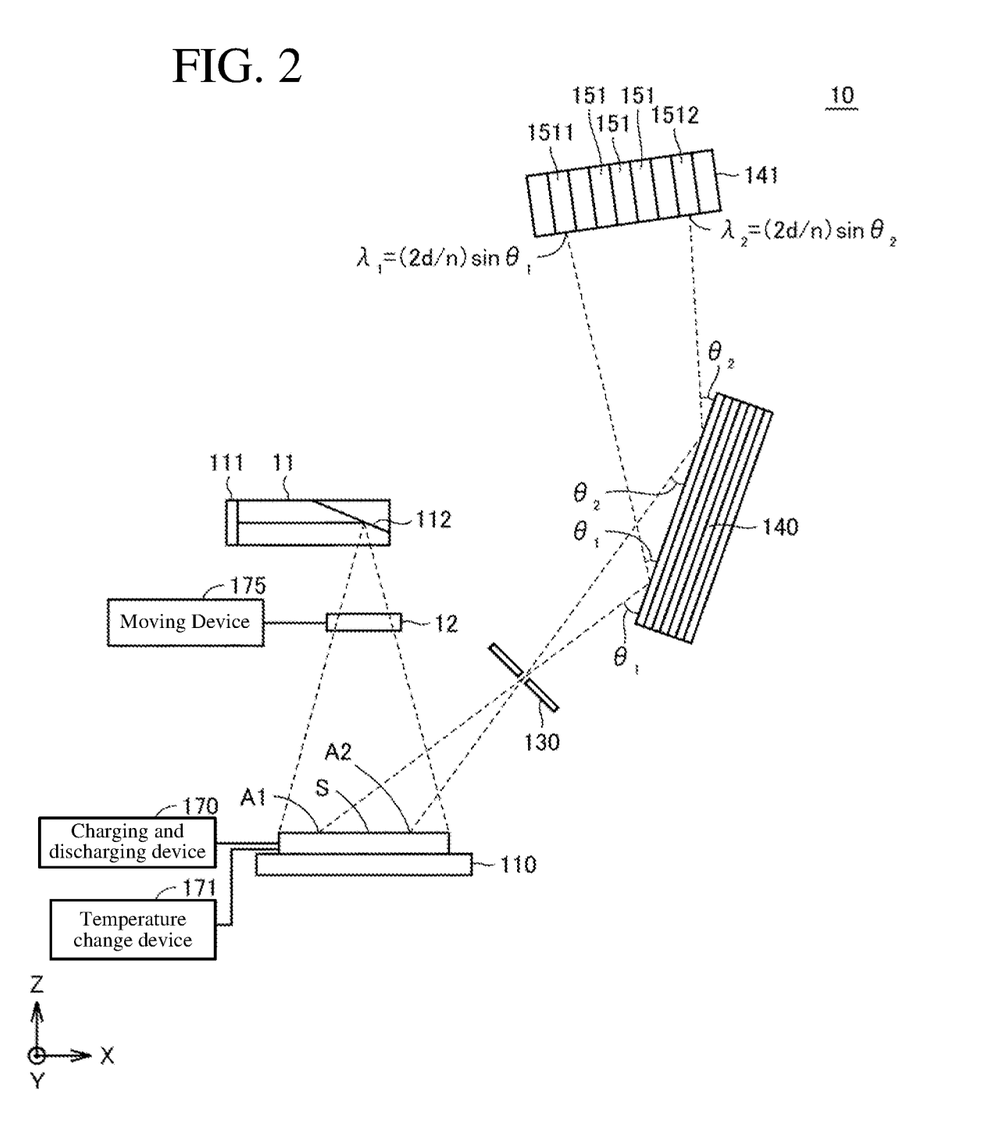
FIG. 2 is a diagram showing a configuration for performing first processing for outputting a valence of a target element of a sample.
Figure 3:
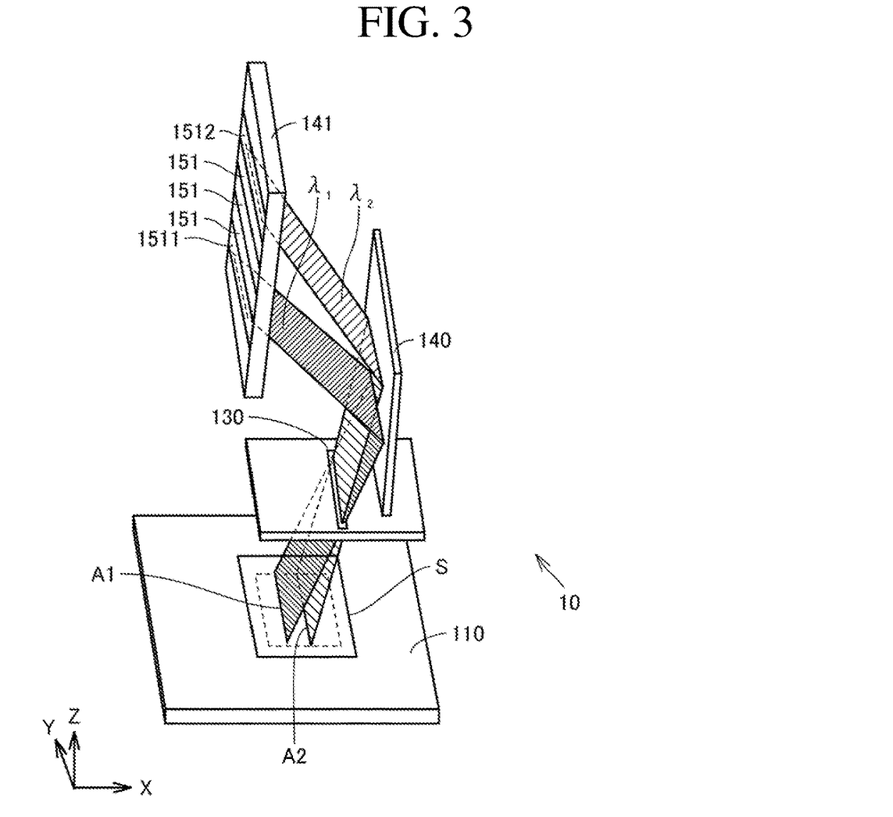
FIG. 3 is a diagram showing a configuration for performing first processing for outputting a valence of a target element of a sample.

Next, among the configurations of the analysis device 100 of this embodiment, the configuration corresponding to the wavelength-dispersive fluorescent X-ray analysis device will be described. FIG. 2 and FIG. 3 are diagrams showing the configuration corresponding to the wavelength-dispersive fluorescent X-ray analysis device.

Referring to FIG. 2 and FIG. 3, the device body 10 has the sample holder 110, the X-ray source 11, the dispersive crystal 140, and the first detector 141, as well as a filter 12, a slit 130, a charging and discharging device 170, a temperature change device 171, and a moving device 175 for moving the filter 12. The dispersive crystal 140 and the first detector 141 constitute a "spectrometer". The charging and discharging device 170 is a device for charging or discharging a secondary battery, for example, when a sample is a secondary battery as described below. The temperature change device 171 changes the temperatures of the sample.

In the dispersive crystal 140, certain crystallographic planes are parallel to the surface of the dispersive crystal 140. Only certain crystal planes can be used to detect characteristic X-rays, and characteristic X-rays Bragg-reflected at other crystal planes can be prevented from being erroneously detected. As shown in FIG. 2, the first detector 141 is composed of a plurality of detection elements 151. The filter 12 is formed of a niobium foil and is disposed between the sample holder 110 and the X-ray source 11. The filter 12 and the moving device 175 will be described later in detail.

As shown in FIG. 2, when X-rays are emitted from the X-ray source 11 onto the sample S in a state in which the sample S is held by the sample holder 110, the X-rays pass through the filter 12, and the characteristic X-rays are emitted from the sample S. The emitted characteristic X-rays have wavelengths which differ depending on the elements constituting the sample S. In FIG. 2, the characteristic X-rays emitted when the X-rays emitted from the X-ray source 11 are emitted to the region from the position A1 to the position A2 pass through the slit 130 to reach the dispersive crystal 140. In FIG. 2, characteristic X-rays occurring at the position A1 and the position A2 are exemplarily indicated by broken lines. The position A2 is located in the positive direction of the X-axis from the position A1.

Further, both the irradiation region at the position A1 and the irradiation region at the position A2 extends in the Y-axis direction (see FIG. 3).

When the angle between the dispersive crystal 140 and the incident characteristic X-rays is θ, the incident angle of the characteristic X-rays is (90-θ) degrees. Because of the angular orientation of the surface of the sample S fixed to the sample holder 110 and the surface of the dispersive crystal 140, the characteristic X-rays emitted at the position A1 are incident on the dispersive crystal 140 at the incident angle (90-$θ_1$) degrees, and the characteristic X-rays emitted at the position A2 are incident on the dispersive crystal 140 at the incident angle (90-$θ_2$) degrees. By causing to pass through the slit 130, the incident angle of the characteristic X-rays to the dispersive crystal 140 can be changed according to the position of the characteristic X-rays in the sample S.

Of the characteristic X-rays incident on the dispersive crystal 140 from the sample S at the incident angle (90-θ) degrees, only the characteristic X-rays having a wavelength satisfying λ=(2d/n)sinθ (λ is a wavelength of a sample, d is a crystal plane distance of the dispersive crystal 140, and n is the order) which is a formula of the Bragg condition are diffracted at the dispersive crystal 140 to reach the first detector 141. In this embodiment, it is configured such that even without moving the slit 130, the dispersive crystal 140, and the first detector 141, only the characteristic X-rays having a wavelength satisfying the formula of the Bragg condition are diffracted by the dispersive crystal 140 and reach the first detector 141.

Since the characteristic X-rays diffracted by the dispersive crystal 140 are emitted at the same angle as the incident angle, the Bragg reflected characteristic X-rays are detected by the detection element 151 located at a position of the plurality of detection elements 151 corresponding to the outgoing angle. Specifically, in the case of FIG. 2, of the characteristic X-rays emitted from the position A1, the characteristic X-rays satisfying the wavelength $λ_1$=(2d/n)sin $θ_1$ is detected by the detection element 1511. Also, of the characteristic X-rays emitted from the position A2, the characteristic X-rays satisfying the wavelength $λ_2$=(2d/n)sin $θ_2$ are detected by the detection element 1512.

Thus, for each of the plurality of detection elements, characteristic X-rays of a wavelength satisfying the Bragg condition of different diffracted angles are detected. In other words, the analysis device can recognize the wavelengths included in the characteristic X-rays by knowing the detection elements at which characteristic X-rays were detected. On the other hand, the wavelength of the characteristic X-rays differs from element to element. Thus, by identifying the detection element at which characteristic X-rays were detected in the first detector 141, the content element of the analysis target sample can be identified.

As described above, the spectrometer of the device body 10 detects the intensities of the respective wavelengths by dispersing the characteristic X-rays generated by the sample S irradiated with the X-rays. The device body 10 transmits the intensity (intensity per detection element) for each detection element to the signal processing device 20. Thereby, the signal processing device 20 can acquire a plurality of wavelengths and the intensities of the characteristic X-rays corresponding to the respective plurality of wavelengths.

The signal processing device 20 converts each of the plurality of acquired wavelengths into energy to acquire a plurality of energies and the intensity of the characteristic X-rays corresponding to each of the plurality of energies. Incidentally, in the energy E and the wavelength λ, the formula E=hc/λ, holds (h is a Planck constant, c is the speed of light). The signal processing device acquires the energy at which the intensity of the characteristic X-ray peak (hereinafter referred to as "peak energy").

The analysis device 100 according to this embodiment can distinguish between Kα X-rays and Kβ X-rays or between Lα X-rays and Lβ X-rays for any element by setting the mean energy resolution to 20 eV or less, preferably 2 eV or less. Thus, the element in the sample can be identified based on the peak energy of at least one of Kα X-rays, Kβ X-rays, Lα X-rays, and Lβ X-rays to be detected, and the element can be quantified based on the intensity of the peak. Here, as the intensity of the peak, the integrated intensity of the peak may be used, or the intensity at the peak top may be used.

Note that the average energy resolution is defined by the value obtained by dividing the difference between the maximum value and the minimum value of the energy of the characteristic X-rays incident on the detector 150 via the irradiated area A of the sample surface through the slit 130 and the dispersive crystal 140 by the number of detection elements of the detector 150.

Even in the same element, some elements having different valences may have different peak energies. For example, the peak energy differs by about 3 eV between divalent Mn and heptavalent Mn. The peak energy differs by about 1.5 eV between zerovalent Cr and trivalent Cr. Therefore, the analysis device 100 of this embodiment detects the valence of the target element based on the peak energy. The signal processing device 20 holds a calibration curve indicating the relationship between the peak energy of the target element and the valence of the target element. The signal processing device detects the valence of the target element by applying the peak energy obtained based on the detection result of the first detector 141 to the calibration curve.

In this embodiment, the valence represents the mean valence of the target element. The mean valence is expressed as the sum of the multiplication values obtained by multiplying the valence of each target element containing the target element and the composition including the target element by the compositional ratio of each material in the sample. For example, in a sample in which Fe, $Fe_3O_4$, and $Fe_2O_3$ are contained, in cases where each composition ratio is P:Q:R, the valence of Fe is 0, the valence of Fe in $Fe_3O_4$ is 2.6667, and the valence of Fe in $Fe_2O_3$ is 3. Therefore, the mean valence is (P×0+Q×2.6667+R×3)/(P+Q+R). Hereinafter, the mean valence is also simply referred to as "valence".

Figure 4:
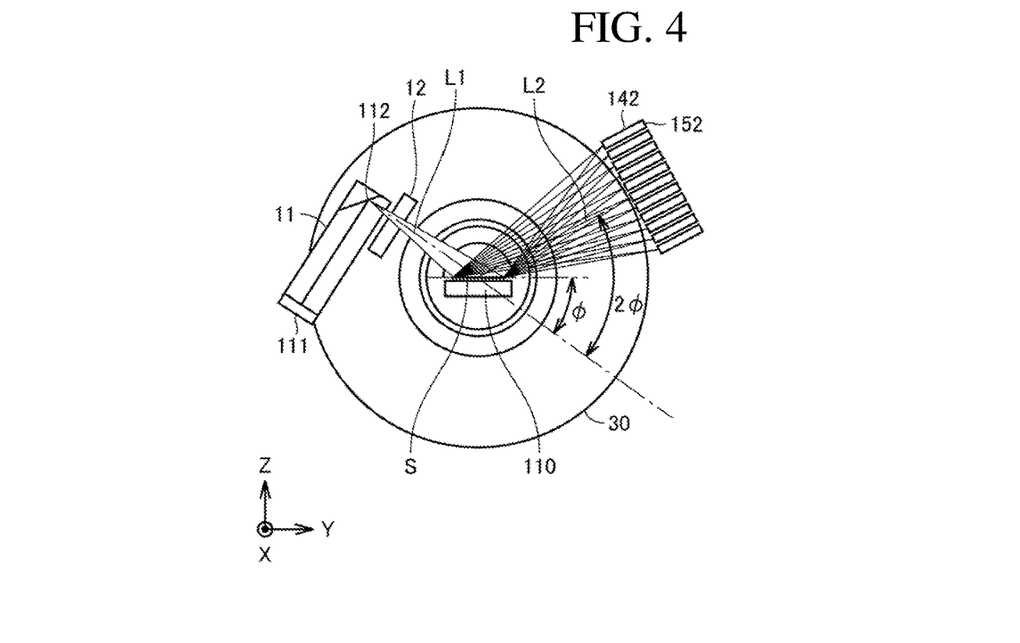
FIG. 4 is a diagram showing a configuration for performing second processing for outputting crystallographic data of a sample (diffraction pattern of a sample).

Next, the detection of the crystallographic data of the sample S will be described. The crystallographic data is information indicating the crystallinity of the sample. In this embodiment, it is a "diffraction pattern" of the sample. FIG. 4 is a diagram for explaining the configuration corresponding to the X-ray diffractometer. The second detector 142 has a plurality (e.g., 1,280) of detection elements 152 arranged side by side in a predetermined orientation. As described above, a filter 12 is disposed between the X-ray source 11 and the sample holder 110.

The goniometer 30 drives the X-ray source 11 and the second detector 142 on the circumference. The goniometer 30 is configured such that the center of the circumference (the rotational center of the goniometer 30) coincides with the center of the sample holder 110 in a plan view as viewed from the Y-Z plane. The goniometer 30 drives the X-ray source 11 on the circumference so as to change the angle φ (first angle) formed by the line L1 connecting the center of the X-ray source and the goniometer 30 and the surface of the sample S. Further, with this driving, the goniometer 30 drives the second detector 142 on the circumference so that the angle φ (second angle) formed by the line L2 connecting the center of the second detector 142 and the rotation center of the goniometer 30 and the surface of the sample S changes while maintaining the same angle φ as the first angle. Note that, as shown in FIG. 4, the angle formed by the extension line of the incident X-rays and the line L2 becomes 2φ.

The goniometer 30 drives the X-ray source 11 so as to increase φ of the incident angle (90-φ) degrees by Δφ at regular intervals. In response, φ of the outgoing angle (90-φ) also increases by Δφ at every constant time. As a result, the angle formed by the extension line of the incident X-rays and the line L2 increases by Δ2φ at every constant time.

Of the X-rays incident on the sample S at incident angle (90-φ) degrees, only the X-rays having the wavelength satisfying λ=(2d/n)sinφ, which is the Bragg condition equation, are diffracted by the sample S and reaches the second detector 142 as diffracted X-rays. "d" denotes the lattice-plane spacing of the crystals of the sample S, "λ" denotes the wavelength of the X-rays from the X-ray source 11, and "n" denotes the order.

The device body 10 transmits the intensity of the diffracted X-rays detected by the second detector 142 and 2φ corresponding to the intensity to the signal processing device 20. The signal processing device 20 can obtain the diffraction pattern of the sample S in which the horizontal axis shows the diffraction angle 2φ and the vertical axis shows the diffraction intensity I. In this diffraction pattern, by analyzing the diffraction angle at which the peak of the diffraction intensity I appears, it is possible to detect the lattice plane spacing d of the crystals of sample S.

Since the analysis device 100 is provided with the goniometer 30, the X-ray source 11 and the second detector 142 can be driven on the circumference. Therefore, it is possible to emit X-rays from the X-ray source 11 to a variety of samples, such as, e.g., powder, a thin film, and a sample hard to be fixed to the sample holder 110.

[Processing of Controller]

Figure 5:
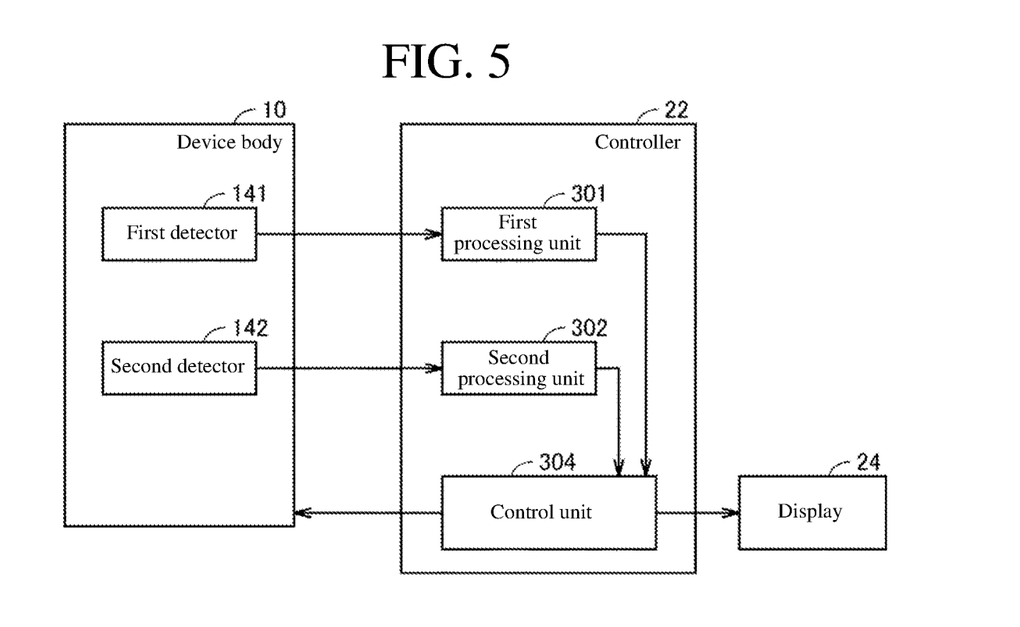
FIG. 5 is a functional block diagram of a controller of a signal processing device.

FIG. 5 is a functional block diagram of the device body 10 and the controller 22 of the signal processing device 20. The controller 22 has a first processing unit 301, a second processing unit 302, and a control unit 304. The first processing unit 301 detects the valence of the target element of the sample based on the intensity for each detection element (intensity for each of the plurality of detection elements) from the first detector 141. The second processing unit 302 detects a diffraction pattern. The first processing unit 301 outputs the valence to the control unit 304. The second processing unit 302 outputs the diffraction pattern to the control unit 304. The control unit 304 displays the result of the processing based on the valence and the diffraction pattern on the display 24.

The analysis device 100 may perform the first processing for detecting the valence of the target element of the sample and the second processing for detecting the crystallographic data of the sample at the same time. Alternatively, it may be configured such that one of the processing of the first processing and the second processing is performed, and the other processing is performed after the completion of the above-described one of the processing.

In the following description, the processing for performing the first processing and the second processing together is referred to as "batch processing," and the processing of performing one of the first processing and the second processing and then performing the other processing after the completion of the above-described one of the processing is referred to as "mode switching processing." The mode for performing the first processing is called "first mode", and the mode for performing the second processing is called "second mode". In the case of the batch processing, there is advantageous in that both the first processing and the second processing of the sample S can be performed under the same conditions. Since the first processing and the second processing can be performed in parallel in the batch processing, the analyzing time can be shortened as compared with the case in which the first processing and the second processing are individually performed as in the mode switching processing. Further, in the mode switching processing, by switching to the first mode or the second mode, the processing load of detecting the valence of the target element of the sample and the processing load of detecting the crystallographic data of the sample can be distributed by the signal processing device 20.

Which of the batch processing and the mode switching processing is performed by the analysis device 100 can be selected by operating the operation unit 26 by the user. In cases where the mode switching processing is selected by the user, the controller 22 may decide which of the first processing and the second processing to be performed first, or the user may decide it.

Figure 6:
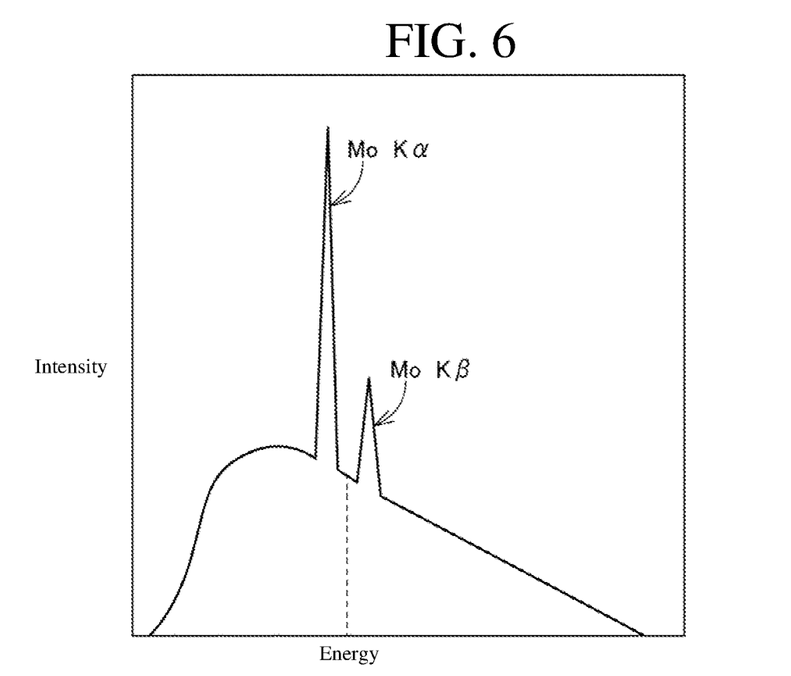
FIG. 6 is an example of an X-ray spectrum when X-rays have not passed through a filter 12.

Next, the filter 12 will be described. The filter 12 is used to selectively pass X-rays of particular wavelengths in the X-rays generated by the X-ray source 11. FIG. 6 shows an example of an X-ray spectrum of X-rays emitted from X-ray source 11 (in the case of not passing through the filter 12). As shown in FIG. 6, the X-rays emitted from the X-ray source 11 include Kα X-rays of molybdenum and Kβ X-rays of molybdenum. In this case, in the sample S, diffraction by the X-rays of two different wavelengths of Kα X-rays and Kβ X-rays may occur, and the detection accuracy by the second detector 142 may deteriorate.

Therefore, in this embodiment, in the case of performing the batch processing (in the case of performing the detection of the valence and the detection of the diffraction pattern at the same time), the control unit 304 controls the moving device 175 to move the filter 12 so that the X-rays from the X-ray source 11 pass through the filter 12 to be emitted to the sample S.

Figure 7:
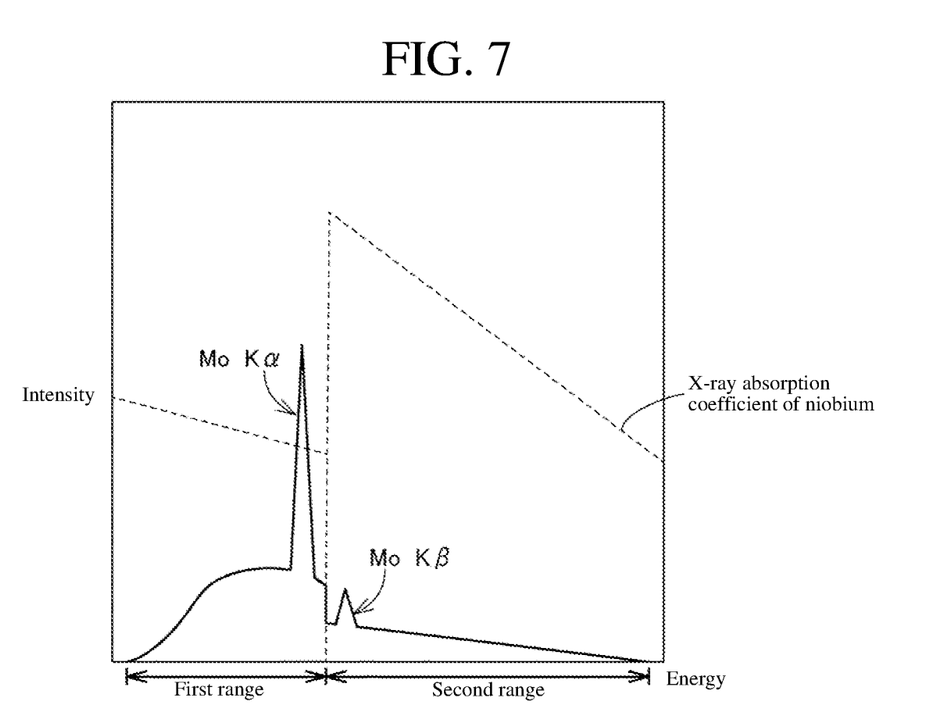
FIG. 7 is an example of an X-ray spectrum when X-rays have passed through a filter 12.

FIG. 7 is an example of an X-ray spectrum in a case where the X-rays from the X-ray source 11 have passed through the filter 12. The dashed line in FIG. 7 shows the X-ray absorptive coefficients of the filter 12 formed of a niobium foil. As shown in FIG. 7, the absorption edge of the filter 12 exists between the peak energy of the molybdenum Kα X-rays and the peak energy of the molybdenum Kβ X-rays. Therefore, the effect of the niobium-absorption edge of the filter 12 reduces the intensity of the Kβ radiation by the molybdenum cathode to a greater extent than the intensity of the Kα radiation by the molybdenum cathode. When the range of the energy smaller than the absorption edge by the filter 12 is denoted as a "first range" and the range of energy larger than the absorption edge by the filter 12 is denoted as a "second range", the filter 12 absorbs the X-rays in the second range more than those in the first range. This artificially enables the monochromatic X-ray diffraction of the Kα X-rays of the molybdenum by the second detector 142.

On the other hand, as shown in FIG. 7, when the X-rays pass through the filter 12, the total amount of energy irradiated by the X-rays is reduced. For this reason, the intensity of the characteristic X-rays emitted from the sample S may sometimes be reduced. In this case, the intensity of the characteristic X-rays detected by the first detector 141 is reduced, and consequently, the detection accuracy of the valence by the signal processing device 20 may sometimes deteriorate. As described above, in the batch processing, there is a concern that the detection accuracy of the valence may deteriorate.

Considering the above, in the case of performing the mode switching processing, the control unit 304 of the controller 22 controls the moving device 175 to move the filter 12 according to the mode. Specifically, the control unit 304 moves the filter 12 to a position where the X-rays from the X-ray source 11 do not pass through when it is controlled to the first mode (in the case of detecting the valence of the target element of the sample S). This prevents the total energy of the X-rays from the X-ray source 11 from decreasing when it is controlled to the first mode. Thus, it is possible to suppress the decrease in the intensity of the characteristic X-rays generated from the sample S. As a result, it is possible to prevent deterioration of the detection accuracy of the valence.

On the other hand, the control unit 304 moves the filter 12 to a position where the X-rays from the X-ray source 11 pass through when it is controlled to the second mode (in the case of detecting the crystallographic data of the sample S). This enables monochromatic X-ray diffraction by the Kα X-rays of molybdenum (see the descriptions of FIG. 6 and FIG. 7).

As described above, in the case of performing the batch processing, the detection accuracy of the valence decreases, but the analysis time can be shortened, whereas in the case of performing the mode switching processing, the detection accuracy of the valence can be prevented from decreasing, but the analysis time becomes longer than the batch processing. Therefore, the user may select either the batch processing or the mode switching processing in view of the analytical duration and the detection accuracy of the valence.

In addition, there may be a configuration in which the user moves the filter 12 according to the mode. However, in this configuration, the burden on the user increases. In this embodiment, since the filter 12 is automatically moved by the control unit 304 according to the mode, the burden on the user is reduced.

Further, in a case where the mode switching processing is selected, in the second mode, as described in FIG. 4, while driving the X-ray source 11 and the second detector 142 by the goniometer 30, the diffracted X-rays are detected by the second detector 142. In the first mode, the X-ray source 11 irradiates the sample S with X-rays without moving the X-ray source 11. Therefore, the radiation angle of the X-rays from the X-ray source 11 is fixed, and therefore the distribution of the X-rays in the plane of the sample S on which the X-rays are incident can be stabilized. Therefore, in the first mode, it is possible to stably generate characteristic X-rays from the sample S, and as a result, it is possible to improve the detection accuracy of the characteristic X-rays by the first detector 141.

Further, in a case where it is controlled to the first mode, the control unit 304 drives the X-ray source 11 at a position where the X-rays is emitted vertical or substantially perpendicular to the main surface of the sample S. As a result, the X-ray dose per unit area of the main surface of the sample can be increased as compared with the case where X-rays are emitted obliquely to the main surface of the sample. This increases the chance that the X-rays will interact with the electrons of the target element, enhancing the excitation of the electrons, which makes it easier for the characteristic X-rays to occur. Note that in a case where it is controlled to the second mode, as described in FIG. 4, the control unit 304 drives the X-ray source 11 and the first detector 141 to satisfy the predetermined positional relation.

[Inspection of Sample]

Next, an example in which the analysis device of this embodiment is used for inspecting a sample will be described. In the field of the material development, in cases where change processing for changing a state of a sample is performed, there is a case in which it is important to grasp how the crystallinity of this sample and the valence of the target element contained in the sample changes. In cases where the first device for measuring the crystallinity and the second device for measuring the valence of the target element are separate, it is necessary to transfer the sample between the two devices. Therefore, it is difficult to perform the measurements of the sample under the same conditions including the time in these two devices.

Also, in the field of the quality inspection, the inspection speed is required, and the sample status may change over time. Therefore, it is not preferable that the inspection delay occurs due to the transfer of the sample from the first device to the second device. Accordingly, in the analysis device of this embodiment, as described above, it is configured such that the detection of the valence of the target element of the sample and the detection of the crystallographic data of the sample can be performed without performing the conveyance of the sample.

An example of the sample of the preferred embodiment is an electrode active material contained in a secondary battery. The electrode active material may be a positive electrode active material or a negative electrode active material. The change processing of this embodiment is the processing of discharging a fully charged secondary battery. The quality of the secondary battery is inspected by causing a conversion reaction of the electrode active material contained in the secondary battery by discharging the fully charged secondary battery. In this embodiment, the sample is an electrode active material containing metal Fe and fluoride of Fe (metal compound). In this case, the target element is "Fe". The conversion reaction of a ferric fluoride-based secondary battery is shown by the following formulas (a) to (c).

1 electron reaction: Fe(III)F$_3$+Li$^+$+$e^-$→LiFe(II)F$_3$     (a)

2 electron reaction: LiFe(II)F$_3$+Li$^+$+$e^-$→LiFe(I)F$_2$+ LiF     (b)

3 electron reaction: LiFe(I)F$_2$+Li$^+$+$e^-$→Fe(0)+2LiF     (c)

When the acceptable secondary battery is fully charged, theoretically, the target element (Fe) of the electrode active material is Fe(III)F$_3$ (see the formula (a)) as shown by the formula (a), and when the secondary battery is fully discharged, the target element (Fe) of the electrode active material becomes Fe(0). That is, the mean valence of the target element (Fe) becomes 0. Further, the diffraction pattern of the electrode active material becomes a diffraction pattern corresponding to the mixed substance of Fe(0)+2LiF. Hereinafter, the tolerance based on the mean valence of 0 is referred to as a normal range of the valence of the target element. Further, the diffraction pattern of Fe(0) of the electrode active material is referred to as a normal diffraction pattern.

However, if the secondary battery is an unacceptable product (for example, the secondary battery has been degraded), the reaction will not sufficiently proceed to the expected reaction of the above-described formula (c), and it becomes a state in which, for example, FeF$_3$, LiFeF$_3$, and LiFeF$_2$ of the formula (a) or (b). In this case, there exist a lot of FeF$_3$, LiFeF$_3$, and LiFeF$_2$, and the average valence of the target element (Fe) may become greater than 0 and not in the normal range. Further, the diffraction pattern of the electrode active material does not become a normal diffraction pattern.

The analysis device 100 can determine whether or not the electrode active material is normal using the valence of the target element and the diffraction pattern of the electrode active material. Specifically, the analysis device 100 discharges the fully charged secondary battery and detects the valence of the target element of the electrode active material of the secondary battery after discharging and the diffraction pattern of the electrode active material of the secondary battery after discharging. The analysis device 100 determines that this secondary battery is "Pass" when the valence of the target element of the electrode active material of the secondary battery after discharging belongs to a predetermined normal range and the diffraction pattern of the electrode active material of the secondary battery after discharging belongs to a predetermined normal range. On the other hand, the analysis device 100 determines that the secondary battery is "Fail" when the valence of the target element of the electrode active material of the secondary battery after discharging does not belong to the normal range, or when the diffraction pattern of the electrode active material of the secondary battery after discharging does not belong to the normal diffraction pattern.

Note that a method is conceivable in which the analysis device discharges the fully charged secondary battery in a fully charged state and inspects the secondary battery by using only the valence of the target element of the electrode active material of the secondary battery after discharging. This is a method in which the valence of the target element of the electrode active material of the secondary battery after discharging is detected, and determines that the secondary battery is "Pass" when the valence is determined to belong to the normal range (e.g., the tolerance based on the mean valence of 0), and that the secondary battery is "Fail" when the valence is determined not to belong to the normal range. However, there is a case in which the crystallographic data (diffraction pattern) of the electrode active material of the secondary battery after discharging is in a normal diffraction pattern. Even in this case, the secondary battery is determined to be "Pass". Therefore, the result of the inspection in this method may not be accurate.

The analysis device of this embodiment can perform the inspection of the sample from two viewpoints of the valence of the target element contained in the sample and the crystallinity (diffraction pattern) of the sample. Therefore, it is possible to improve the inspection accuracy of the secondary battery as compared with the "analysis device for inspecting secondary battery by using only the valence of the target element of the electrode active material of the secondary battery after discharging".

In the analysis device according to this embodiment, it is configured to perform both the first processing for detecting the valence of the target element and the second processing for detecting the crystallographic data of the electrode active material with one device. Therefore, as compared with the configuration in which a first device for performing first processing and a second device for performing second processing are separate devices, it is not necessary to transfer the sample between the devices, so that the time required for the analyzing processing can be shortened. In addition, in the analysis device of this embodiment, since the first processing for detecting the valence of the target element of the sample and the second processing can be performed in parallel, the sample can be analyzed under the same conditions.

Figure 8:
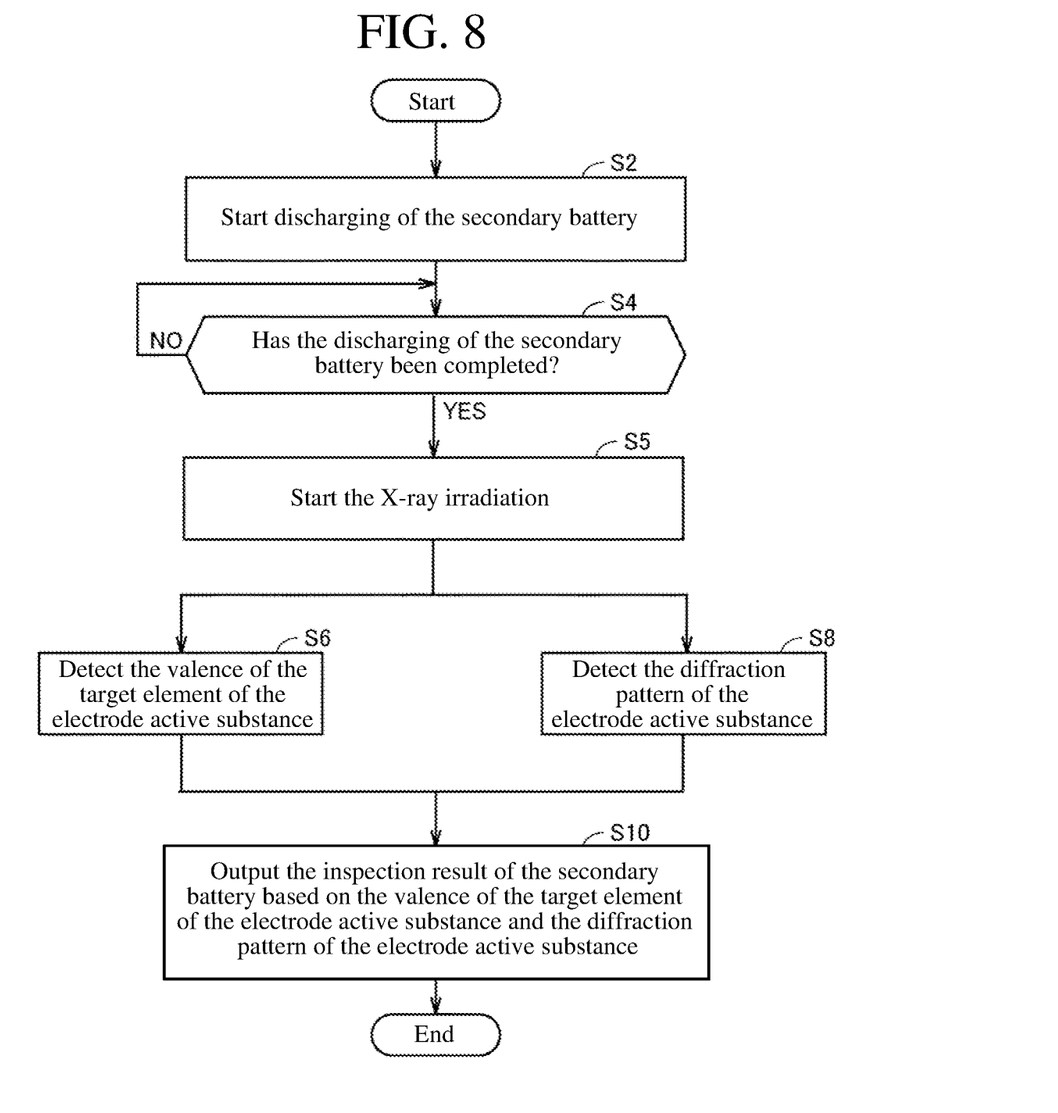
FIG. 8 is an example of a flowchart showing processing of a controller when a sample is a secondary battery.

FIG. 8 is a flowchart for explaining the detailed deterioration diagnostic processing of a secondary battery described above, which is performed in the controller 22. The processing of FIG. 8 is initiated when the user performs the operation on the operation unit 26 to cause the analysis device 100 to initiate a secondary battery inspection.

In Step S2, the control unit 304 of the controller 22 starts discharging of the secondary battery by controlling the charging and discharging device 170. Next, in Step S4, the control unit 304 determines whether or not the discharging of the secondary battery has been completed. As for the determination on whether or not the discharging has been completed, for example, the control unit 304 measures the remaining amount of the secondary battery and determines that the discharging has been completed when the remaining amount of the battery has become less than a predetermined amount. Alternatively, the control unit 304 may determine that the discharging has been completed when a predetermined period has elapsed since the discharging was started. The processing of Step S4 will be repeated until discharging is completed. When the discharging is completed, in Step S5, the control unit 304 starts irradiation of the sample with X-rays.

In Step S6, the first processing unit 301 of the controller 22 detects the valence of the target element (Fe) of the electrode active material of the secondary battery after discharging. In Step S8, the second processing unit 302 of the controller 22 detects the diffraction pattern of the electrode active material of the sample after discharging.

When the above-described batch processing is selected, the control unit 304 of the controller 22 performs the processing of Step S6 and the processing of Step S8 together. When the above-described mode switching processing is selected, the control unit 304 of the controller 22 first performs one of the processing of Step S6 and the processing of Step S8, and after completing the one processing, performs the other processing.

Next, in Step S10, the controller 22 outputs the inspection result of the secondary battery based on the valence of the target element of the electrode active material of the secondary battery after discharging and the crystallographic data of the electrode active material of the secondary battery after discharge. Specifically, the control unit 304 determines whether or not the valence of the electrode active material of the secondary battery after discharging belongs to the normal range.

The control unit 304 determines whether or not the diffraction pattern of the electrode active material of the secondary battery after discharging is a normal diffraction pattern. The control unit 304 determines that this secondary battery is "Pass" when the valence of the target element of the electrode active material of the secondary battery after discharging belongs to the normal region and the diffraction pattern of the electrode active material of the secondary battery after discharging belongs to the normal diffraction pattern. On the other hand, the control unit 304 determines that this secondary battery is "Fail" when the valence of the target element of the electrode active material of the secondary battery after discharging does not belong to the normal range, or when the diffraction pattern of the secondary battery of the electrode active material of the secondary battery after discharging is not the normal diffraction pattern. The control unit 304 outputs the result of the "Pass/Fail". In this embodiment, the control unit 304 displays the result of the "Pass/Fail" on the display 24. The output of the "Pass/Fail" result may be performed by another processing. For example, the inspection result may be printed on a sheet and the sheet may be output.

As described above, the analysis device 100 of this embodiment can perform the inspection of the sample from two viewpoints of the valence of the target element contained in the sample and the crystallographic data (diffraction pattern) of the sample. Therefore, the analysis device 100 can enhance the inspection accuracy of the sample In addition, an X-ray diffractometer and a wavelength-dispersive X-ray fluorescence analysis device alone have already been put into practical use as a device that is smaller than the SPring-8. Therefore, by utilizing the same mechanisms as those described above, it is possible to detect the valence of the target element contained in the sample and the crystallographic data of the sample with a device which is smaller than the SPring-8

In the embodiment described above, the configuration in which the secondary battery status change processing for checking the secondary battery is the discharging processing has been explained. However, the change processing may be another processing. For example, the change processing may be processing that charges the secondary battery. In this case, the "Pass/Fail" of the secondary battery can be determined by the valence and the diffraction pattern of the target element of the electrode active material after charging determine.

The change processing may be processing in which the temperature change device 171 (see FIG. 2) changes the temperatures of the electrode active material of the secondary battery. The temperature change may be processing for increasing the temperature or decreasing the temperature.

In a fully-charged secondary battery determined as "Pass", in a proper operating temperature, the electrode active material reacts as in the formulas (a) to (c). Therefore, the valence of the target element (Fe) becomes 0, and the diffraction pattern of the electrode active material becomes a pattern corresponding to the mixed substance of Fe(0)+ 2LiF. Hereinafter, the tolerances based on 3 will be referred to as a normal range of a valence of a target element. Also, the diffraction pattern of Fe(0)+2LiF of the electrode active material will be referred to as a normal diffraction pattern.

However, in a case where the secondary battery is a failed product (e.g., the secondary battery is weak at low temperatures), the expected reaction may not proceed well to the above-described formula (c). For example, it becomes a mixture of $FeF_3$, $LiFeF_3$, and $LiFeF_2$ of the formula (a) or (b). In this case, there exist many $FeF_3$, $LiFeF_3$, and $LiFeF_2$, and the average valence of the target element (Fe) can be greater than 0 and does not belong to normal range. Further, the diffraction pattern of the electrode active material will not become a normal diffraction pattern.

Therefore, when the valence of the target element of the electrode active material after the temperature change belongs to the normal range and the diffraction pattern of the electrode active material after the temperature change is in the normal diffraction pattern, the control unit 304 determines that secondary battery is "Pass". On the other hand, when the valence of the target element of the electrode active material after the temperature change does not belong to the normal range, or when the diffraction pattern of the electrode active material after the temperature change is not in the normal diffraction pattern, the control unit 304 determines that secondary battery is "Fail".

The change processing (change processing of the electrode active material, which is a sample) of the secondary battery may include at least two of the charge processing of the secondary battery, a discharge processing of the secondary battery, and a temperature change processing of the secondary battery. Further, the analysis device 100 may perform the change processing of the secondary battery a plurality of times. In the plurality of times of the change processing, it may be configured such that the number of times the secondary battery determined to be "Pass" is counted, and the control unit 304 determines that the secondary battery is "Pass" when the counted number of times is equal to or greater than a predetermined number.

With the above-described configuration, the analysis device 100 can inspect the secondary battery based on the two viewpoints: the valence of the target element of electrode active material of the secondary battery and the crystallographic data of the electrode active material of the secondary battery.

In addition, in the above-described embodiment, an example in which the sample is a secondary battery has been described, but the sample may be another substance. For example, a catalyst may be used as a sample. A catalyst is placed, for example, in a chamber (not shown). For example, when a catalyst is a platinum catalyst, the target element is Pt.

Figure 9:
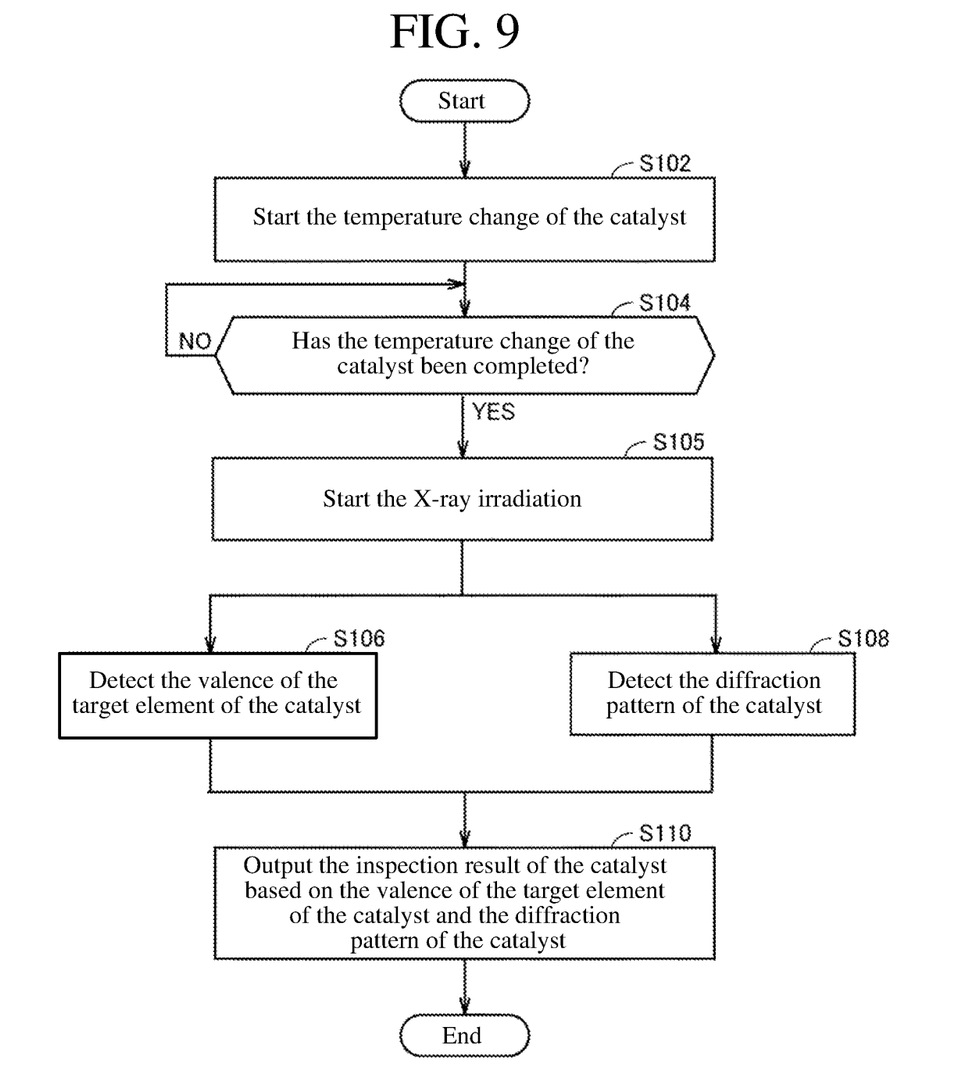
FIG. 9 is an example of a flowchart showing processing of the controller when a sample is a catalyst.

FIG. 9 is an example of a flowchart showing the processing of the controller 22 when the sample is a catalyst. In Step S102, the control unit 304 of the controller 22 starts changing the temperature of the catalyst by controlling the temperature change device 171. Next, in Step S104, the control unit 304 determines whether or not the change in the temperature of the catalyst has been completed. The processing of Step S104 is repeated until the temperature change of the catalyst is completed. When the change of the temperature of the catalyst has been completed, in Step S105, the control unit 304 starts irradiation of X-rays.

In Step S106, the first processing unit 301 of the controller 22 detects the valence of the target element of the catalyst after the temperature change. In Step S108, the second processing unit 302 of the controller 22 detects the diffraction pattern of the catalyst after the temperature change.

Next, in Step S110, the controller 22 outputs the inspection result of the catalyst based on the valence of the target element after the temperature change and the crystallographic data of the catalyst after the temperature change. Specifically, the control unit 304 determines whether or not the valence of the target element of the catalyst after the temperature change belongs to a predetermined normal range. In addition, the control unit 304 determines whether or not the diffraction pattern of the catalyst after the temperature change is a normal diffraction pattern. When the valence of the target element of the catalyst after the temperature change belongs to the normal range and the diffraction pattern of the catalyst after the temperature change is a normal diffraction pattern, the control unit 304 determines that the catalyst is "Pass". On the other hand, when the valence of the target element of the catalyst after the temperature change does not belong to a normal range, or when the diffraction pattern of the catalyst after the temperature change is not a normal diffraction pattern, the catalyst is determined as "Fail". The control unit 304 outputs the result of the "Pass/Fail".

As described above, the analysis device 100 of this embodiment can perform an inspection of a catalyst from two viewpoints: the valence of the target element of the catalyst and the crystallographic data (diffraction pattern) of the catalyst. Therefore, the analysis device 100 can enhance the accuracy of the catalyst inspection.

In the above-described embodiment, the configuration has been described in which the change processing of the state of the catalyst for inspecting the catalyst is the temperature change processing of the catalyst. However, the change processing may be another processing. For example, the change processing may be processing for oxidizing the catalyst. In a case where this configuration is employed, the control unit 304 determines that this catalyst is "Pass" when the valence of the target element contained in the oxidized catalyst belongs to a normal range and the diffraction pattern of the oxidized catalyst is a normal diffraction pattern. On the other hand, the control unit 304 determines that the catalyst is "Fail" when the valence of the target element contained in the oxidized catalyst does not belong to a normal range, or when the diffraction pattern of the oxidized catalyst is not a normal diffraction pattern, Further, the change processing may be processing for reducing the catalyst. In a case where this configuration is adopted, the control unit 304 determines that this catalyst is "Pass" when the valence of the target element contained in the catalyst after the reduction belongs to a normal range and the diffraction pattern of the catalyst after reduction is a normal diffraction pattern. On the other hand, the control unit 304 determines that this catalyst is "Fail" when the valence of the target element contained in the catalyst after reduction does not belong to a normal range, or when the diffraction pattern of the catalyst after reduction is not a normal diffraction pattern.

The change processing of the catalyst may include at least two processing between the temperature change processing of the catalyst, the processing for oxidizing the catalyst, and the processing for reducing the catalyst. In addition, the analysis device 100 may perform the change processing of the catalyst a plurality of times. In performing the change processing a plurality of times, the number of times that the catalyst is determined to be "Pass", when the counted number of times is equal to or larger than a predetermined number of times, the control unit 304 may output that it is "Pass".

With the above-described configuration, the analysis device 100 can inspect the catalyst based on two viewpoints: the valence of the target element and the crystallographic data of catalyst.

Further, the analysis device 100 may also inspect the sample based on: the valence and the diffraction pattern before performing the change processing to the sample; and the valence and the diffraction pattern after performing the change processing to the sample. The analysis device 100 may inspect the sample based on: for example, the difference between the valence before performing the change processing for the sample and the valence after performing the change processing for the sample, and the difference pattern between the diffraction pattern before performing the change processing for the sample and the diffraction pattern after performing the change processing for the sample.

[Others]

(1) In this embodiment, the description has been made such that the shapes and the arrangements of the X-ray source 11, the dispersive crystal 140, and the first detector 141 for performing the first processing for outputting the valence of the target element of the sample are as shown in FIG. 3. However, the shapes and the arrangements of these components are not limited to the example shown in FIG. 3, and other shapes and arrangements may be used. For example, the shape and the arrangement of these components may be so-called Roland circles.

(2) In this embodiment, the description has been made such that the analysis device 100 has the goniometer 30. However, the analysis device 100 may not have the goniometer 30. In this case, although the range of φ that can be measured becomes small and it becomes difficult to cope with various sample, such as, e.g., powder, a thin film, and a sample that is difficult to fix to the sample holder 110, the size of the apparatus can be reduced.

(3) In the above-described embodiment, the configuration has been described in which the secondary battery to be inspected is an iron-fluoride-based secondary battery. However, the secondary battery to be inspected may be another secondary battery, for example, an iron-oxide-based secondary battery. The conversion reactions of the iron-oxide-based the secondary battery are shown by the following formulas (d) to (f).

$$1 \text{ electron reaction: } Fe(III)_2O_3 + 2Li^+ + 2e^- \rightarrow Li_2Fe(II)_2O_3 \quad (d)$$

$$2 \text{ electron reaction: } Li_2Fe(II)_2O_3 + 2Li^+ + 2e^- \rightarrow 2LiFe(I)O + Li_2O \quad (b)$$

$$3 \text{ electron reaction: } 2LiFe(I)O + 2Li^+ + 2e^- \rightarrow 2Fe(0) + 2Li_2O \quad (c)$$

Even if the secondary battery to be inspected is the above-described iron oxide-based secondary battery, the analysis device 100 can inspect the iron oxide-based secondary battery as the sample to be an electrode active material of the iron oxide-based secondary battery.

(4) In the above-described embodiment, the configuration has been described in which the analysis device 100 performs the inspection of a sample (an electrode active material or a catalyst, etc.) based on the crystallographic data. However, the analysis device 100 may perform other processing based on the crystallographic data. The above-described other processing is, for example, the processing for identifying the substance contained in the sample. In a case where the configuration is employed, the diffraction patterns of a plurality of known substances are stored in a predetermined storage area. The control unit 304 compares the diffraction pattern acquired from the device body 10 with the diffraction pattern of a plurality of known substances, thereby identifying the substances contained in the sample. Thus, the analysis device 100 allows the user to select which of: the inspection of the sample based on the diffraction pattern and the identification of the substance contained in the sample based on the diffraction pattern. Thus, the user usability can be improved.

[Aspects]

It will be understood by those skilled in the art that the plurality of exemplary embodiments described above is illustrative of the following aspects.

(Item 1)

An analysis device according to one aspect of the present invention includes:

an X-ray source configured to emit X-rays to a sample;
a first detector configured to detect characteristic X-rays generated from the sample by X-ray irradiation;
a second detector configured to detect X-rays diffracted by the sample; and
a signal processing device,
wherein the signal processing device is configured to:
detect a valence of a target element of the sample based on the characteristic X-ray detected by the first detector; and
detect crystallographic data of the sample based on the X-rays detected by the second detector.

According to the analysis device as recited in the above-described item 1, it is possible to detect the crystallographic data of the sample together with the valence of the sample while reducing the size of the device.

(Item 2)

According to the analysis device as recited in the first item, the signal processing device performs processing for detecting the valence of the target element of the sample and processing for detecting the crystallographic data of the sample together.

According to the analysis device of the item 2, it is possible to perform the detection of the valence of the target element of the sample and the detection of the crystallographic data of the sample in a short time.

(Item 3)

The analysis device as recited in the above-described item 2 further includes:
- a filter configured to absorb more X-rays in a second range than X-rays in a first range, the second range having the energy larger than the first range,
- wherein the X-rays from the X-ray source pass through the filter to be emitted to the sample.

According to the analysis device as recited in the term 3, it is possible to prevent the decrease in the detection accuracy due to the second detector caused by the diffraction by the X-rays of a plurality of different wavelengths.

(Item 4)

In the analysis device as recited in the above-described item 1,
- the signal processing device controls to either
- a first mode for detecting the valence of the target element of the sample, or
- a second mode for detecting the crystallographic data of the sample.

According to the analysis device of the above-described item 4, it is possible to disperse the processing load for detecting the valence of the target element and the processing load for detecting the crystallographic data of the sample (Item 5)

In the analysis device as recited in the above-described item 4, it further includes:
- a filter configured to absorb more X-rays in a second range than X-rays in a first range, the second range having the energy larger than the first range,
- wherein in the first mode, the X-rays are emitted to the sample without passing through the filter, and
- wherein in the second mode, the X-rays pass through the filter and to be emitted to the sample.

According to the analysis device as recited in the above-described item 5, while preventing the decrease in the detection accuracy in the second detector caused by the occurrence of the diffraction by the X-rays of a plurality of different wavelengths, it is possible to prevent the decrease in the detection accuracy in the first detector due to the decrease in the intensity of the X-rays in the first range.

(Item 6)

The analysis device as recited in the above-described item 5, further includes:
- a moving unit configured to move the filter to a position where X-rays do not pass through when controlled to the first mode and move the filter to a position where X-rays pass through when controlled to the second mode.

According to the analysis device as recited in the above-described item 6, since the filter is automatically moved in accordance with the mode, the burden on the user can be reduced.

(Item 7)

In the analysis device as recited in any one of the above-described items 4 to 6, in the first mode, the X-rays from the X-ray source are emitted perpendicularly or substantially perpendicularly to a main surface of the sample.

According to the analysis device as recited in the item 7, the X-rays per unit area of the main surface of the sample can be increased. Thus, since the electrons are easily excited, the characteristic X-ray is likely to occur.

(Item 8)

The analysis device as recited in any one of the above-described items 4 to 7, further includes:
- a driving unit configured to move the X-ray source and the second detector such that an incident angle and an outgoing angle of the X-rays relative to the sample become equal to each other,
- wherein in the first mode, the driving unit does not move the X-ray source and the second detector, and
- wherein in the second mode, the driving unit moves the X-ray source and the second detector.

According to the analysis device as recited in the item 8, since the X-ray source stops in the first mode, the characteristic X-rays can be stably generated from the sample S, and as a result, the accuracy of detecting the characteristic X-rays by the first detector 141 can be improved.

(Item 9)

The analysis device as recited in any one of the above-described item 1 to 7, further includes:
- a driving unit configured to move the X-ray source and the second detector such that an incident angle and an outgoing angle of the X-rays relative to the sample become equal to each other.

According to the analysis device as recited in the above-described item 9, a variety of samples, such as, e.g., powder, a thin film, or a sample which is difficult to fix to the sample holder 110, can be irradiated with the X-ray source.

(Item 10)

In the analysis device as recited in the above-described items 3 or 5,
- wherein the X-ray source is configured by a molybdenum cathode, and
- wherein the filter is configured by a foil made of niobium.

According to the analysis device as recited in the above-described term 10, it is advantageous that the X-rays can be monochromatized artificially.

(Item 11)

The analysis device as recited in any one of the above-described items 1 to 10, further includes:
- a change device configured to perform change processing for changing a state of the sample,
- wherein the signal processing device inspects the sample based on the valence of the sample and the crystallographic data of the sample after the state of the sample has been changed by the change device.

According to the analysis device of the above-described eleventh item, it is possible to inspect the sample from two viewpoints of the valence of the sample and the crystallographic data of sample.

(Item 12)

In the analysis device as recited in the above-described item 11,
- wherein the sample is an electrode active material contained in a secondary battery, and
- wherein the change processing includes at least one of charging processing of the secondary battery, discharging processing of the secondary battery, and processing of changing a temperature of the secondary battery.

According to the analysis device as recited in the above-described item 12, it is possible to inspect the secondary battery from the two view points of the valence of the electrode active material contained in the sample and the crystallographic data of the sample.

(Item 13)

The analysis device as recited in the above-described item 11,
wherein the sample is a catalyst, and
wherein the change processing includes at least one of processing for changing an oxidation state of the catalyst, processing for changing a reduction state of the catalyst, and processing for changing a temperature of the catalyst.

According to the analysis device as recited in the above-described item 13, the catalyst can be inspected from the two viewpoints of the valence of the catalyst and the crystallographic data of the sample.

(Item 14)

An analysis method according to another aspect of the present invention, includes:
a step of irradiating a sample with X-rays;
a step of detecting a valence of a target element of the sample based on characteristic X-rays generated from the sample by X-ray irradiation; and
a step of detecting crystallographic data of the sample based on the X-rays diffracted by the sample.

According to the analysis method as recited in the above-described Item 14, it is possible to detect the crystallographic data of the sample together with the valence of the sample while miniaturizing the size of the analysis device used in this analysis method.

(Item 15)

The analysis method as recited in the above-described item 14, further includes:
a step of changing a state of the sample; and
a step of inspecting quality of the sample based on the valence of the sample and the crystallographic data of the sample after the state of the sample has been changed.

According to the analysis method of the above-described item 15, the sample can be inspected from the two viewpoints of the valence of the sample and the crystallographic data of the sample.

In addition, with respect to the above-described embodiments and modified examples, it is planned from the beginning of the application that the configurations described in the embodiments are appropriately combined within a range in which disadvantage or inconsistency does not occur, including combinations not mentioned in the specification.

The embodiments disclosed herein are to be considered in all respects as illustrative and not restrictive. The scope of the present invention is indicated by the appended claims rather than by the above-described foregoing descriptions and is intended to include all modifications within the meanings and ranges equivalent to the scope of the claims.

DESCRIPTION OF SYMBOLS

10: Device body
11: X-ray source
12: Filter
20: Signal processing device
22: Controller
24: Display
26: Operation unit
30: Goniometer
31: Processor
32: Memory
100: Analysis device
110: Sample holder
130: Slit
140: Dispersive crystal
141: First detector
142: Second detector
150: Detector
170: Charging and discharging device
171: Temperature change device
175: Moving device
301: First processing unit
302: Second processing unit

The invention claimed is:

1. An analysis apparatus comprising:
an X-ray source configured to emit X-rays toward a sample;
a first detector configured to detect characteristic X-rays generated from the sample by X-ray irradiation;
a second detector configured to detect X-rays diffracted by the sample; and
a signal processing device,
wherein the signal processing device is configured to:
detect a valence of a target element of the sample based on the characteristic X-rays detected by the first detector; and
detect crystallographic data of the sample based on the X-rays detected by the second detector.

2. The analysis device as recited in claim 1,
wherein the signal processing device performs processing for detecting the valence of the target element of the sample and processing for detecting the crystallographic data of the sample together.

3. The analysis device as recited in claim 2, further comprising:
a filter configured to absorb more X-rays in a second range than X-rays in a first range, the second range having the energy larger than the first range,
wherein the X-rays from the X-ray source pass through the filter to be emitted to the sample.

4. The analysis device as recited in claim 1,
wherein the signal processing device controls to either
a first mode for detecting the valence of the target element of the sample, or
a second mode for detecting the crystallographic data of the sample.

5. The analysis device as recited in claim 4, further comprising:
a filter configured to absorb more X-rays in a second range than X-rays in a first range, the second range having the energy larger than the first range,
wherein in the first mode, the X-rays are emitted to the sample without passing through the filter, and
wherein in the second mode, the X-rays pass through the filter to be emitted to the sample.

6. The analysis device as recited in claim 5, further comprising:
a moving unit configured to move the filter to a position where X-rays do not pass through when controlled to the first mode and move the filter to a position where X-rays pass through when controlled to the second mode.

7. The analysis device as recited in claim 4,
wherein in the first mode, the X-rays from the X-ray source are emitted perpendicularly or substantially perpendicularly to a main surface of the sample.

8. The analysis device as recited in claim 4, further comprising:
a driving unit configured to move the X-ray source and the second detector such that an incident angle and an outgoing angle of the X-rays relative to the sample become equal to each other,
wherein in the first mode, the driving unit does not move the X-ray source and the second detector, and
wherein in the second mode, the driving unit moves the X-ray source and the second detector.

9. The analysis device as recited in claim 1, further comprising:
a driving unit configured to move the X-ray source and the second detector such that an incident angle and an outgoing angle of the X-rays relative to the sample become equal to each other.

10. The analysis device as recited in claim 3,
wherein the X-ray source is configured by a molybdenum cathode, and
wherein the filter is configured by a foil made of niobium.

11. The analysis device as recited in claim 1, further comprising:
a change device configured to perform change processing for changing a state of the sample,
wherein the signal processing device inspects the sample based on the valence of the sample and the crystallographic data of the sample after the state of the sample has been changed by the change device.

12. The analysis device as recited in claim 11,
wherein the sample is an electrode active material contained in a secondary battery, and
wherein the change processing includes at least one of charging processing of the secondary battery, discharging processing of the secondary battery, and processing of changing a temperature of the secondary battery.

13. The analysis device as recited in claim 11,
wherein the sample is a catalyst, and
wherein the change processing includes at least one of processing for changing an oxidation state of the catalyst, processing for changing a reduction state of the catalyst, and processing for changing a temperature of the catalyst.

14. An analysis method comprising:
a step of irradiating a sample with X-rays;
a step of detecting a valence of a target element of the sample based on characteristic X-rays generated from the sample by X-ray irradiation; and
a step of detecting crystallographic data of the sample based on the X-rays diffracted by the sample.

15. The analysis method as recited in claim 14, further comprising:
a step of changing a state of the sample; and
a step of inspecting quality of the sample based on the valence of the sample and the crystallographic data of the sample after the state of the sample has been changed.

* * * * *